ically Q-Switched Nd:YAG Laser Irradiation", *J. Dent. Res.*, 59(2): 137, Feb., 1980.

United States Patent [19]
Higuchi et al.

[11] Patent Number: 4,877,401
[45] Date of Patent: Oct. 31, 1989

[54] METHOD OF PREVENTING TOOTH DECAY BY LASER BEAM IRRADIATION AND CHEMICAL TREATMENT

[75] Inventors: William I. Higuchi; Jeffrey I. Fox; G. Lynn Powell, all of Salt Lake City, Utah

[73] Assignee: University of Utah, Salt Lake City, Utah

[21] Appl. No.: 165,807

[22] Filed: Mar. 9, 1988

[51] Int. Cl.$^4$ ............................ A61K 6/00; A61K 7/16
[52] U.S. Cl. ........................................ 433/215; 106/35; 424/54; 433/216; 433/217.1
[58] Field of Search ...................... 433/215, 216, 217.1; 106/35; 424/54

[56] References Cited

U.S. PATENT DOCUMENTS

| | | | |
|---|---|---|---|
| 3,897,548 | 7/1975 | Katz | 424/54 |
| 4,273,535 | 6/1981 | Yamamoto et al. | 433/216 |
| 4,934,002 | 1/1976 | Haefele | 424/54 |

OTHER PUBLICATIONS

Stern, R., "Dentistry and the Laser", *Laser Applications in Medicine and Biology*, vol. 2, (Ed. M. Wolbarsht), Plenum Press, N.Y., 1974.
CA 108(15): 124470w, Nakayama et al., 1987.
CA 107(3): 20048c, Nelson et al., 1987.
CA 98(25): 21223y, Suzuki et al., 1982.
CA 98(13): 10359c, Tomita et al., 1982.
CA 69(14): 54291p, Proctor & Gamble, (GB 1110987), 1968.
Stern, et al., "Laser Enamel: Ultrastructural Observations of Pulsed Carbon Dioxide Laser Effects", *J. Dent. Res.*, 51(2): 455–460, Mar.–Apr. 1972.
Yamamoto, et al., "Prevention of Dental Caries by Acoucsto-Optically Q-Switched Nd:YAG Laser Irradiation", *J. Dent. Res.*, 59(2): 137, Feb., 1980.
Yamamoto, et al., "Potential of Yttrium-Aluminum-Garnet Laser in Caries Prevention", *J. Oral Path.*, 1974:3: 7–15.
Nelson, et al., "Artificial Lesion Formation After Low Energy Infrared Laser Irradiation", *IADR/AADR Abstracts*, 1985, Abstract no. 1712, p. 365.

*Primary Examiner*—Paul Lieberman
*Assistant Examiner*—Linda D. Skaling
*Attorney, Agent, or Firm*—Trask, Britt & Rossa

[57] ABSTRACT

A method for preventing tooth decay comprising: (1) laser irradiation of the tooth's surface with a carbon dioxide laser (wavelength=10.6 microns) at 20 to 50 watts for 1 to 400 seconds, and (2) subsequent chemical treatment of the tooth with a chemical agent such as ethane-1-hydroxy-1, 1-diphosphonic acid at concentrations greater than about 0.00001 molar. The resulting tooth has a reduced dissolution rate in acid and increased resistivity to cavities.

8 Claims, 2 Drawing Sheets

METHOD OF PREVENTING TOOTH DECAY BY LASER BEAM IRRADIATION AND CHEMICAL TREATMENT

BACKGROUND OF THE INVENTION

1. Field

This invention relates to a method for preventing tooth decay.

2. State of the Art

Several methods, compositions, and devices have been described for preventing dental caries or cavities.

U.S. Pat. No. 4,273,535 to Yamamoto et al. describes a device and method for preventing tooth decay by the use of high speed, repetitious pulses of laser beams projected from a Q-switched continuous excitation Nd:YAG laser through a glass beam guide. Yamamoto et al. also discloses coating the tooth immediately before the laser treatment with a fluorine compound.

Two articles by Yamamoto and other co-workers disclose similar results using the Nd:YAG laser. Yamamoto and Sato, "Prevention of Dental Caries by Acousto-Optically Q-Switched Nd:YAG Laser Irradiation," *Journal of Dental Research*, 59(2): 137, February 1980, and Yamamoto and Ooya, "Potential of Yttrium-Aluminum-Garnet Laser in Caries Prevention," *J. Oral Path.*, 3:7-15, 1974.

Stern et al., "Lased Enamel: Ultrastructural Observations of Pulsed Carbon Dioxide Laser Effects," *Journal of Dental Research*, 52(1): 455-460, January-February 1972, discloses the use of a pulsed carbon dioxide ($CO_2$) laser on human enamel support. The laser irradiated enamel exhibited greater acid resistance than non-irradiated enamel.

Abstract No. 1712 of the IA DR/AADR ABSTRACTS 1985 on page 365 describes work by Nelson et al. using a line tunable ($CO_2$) gas laser. These workers concluded that specific frequency, low energy density, infrared laser irradiation is an effective caries preventive measure in the laboratory situation.

U.S. Pat. No. 3,934,002 to Haefele discloses oral compositions containing a certain bis-biguanide compound to inhibit the formation of dental plaque and caries, and anti-calculus agents to inhibit stain formation of the teeth by the bis-biguanide compound. Ethane-1-hydroxy-1,1-diphosphonic acid ("EHDP") is an especially preferred anti-calculus agent.

U.S. Pat. No. 3,897,548 to Katz discloses a composition useful in retarding the formation of dental plaque, and thus the formation of dental caries, comprising an antibacterial agent in combination with an enamel conditioning agent to facilitate incorporation of the antibacterial agent into the dental enamel. A preferred enamel conditioning agent is EHDP.

SUMMARY OF THE INVENTION

The invention comprises a method for treating the surface of an animal's tooth to prevent dental caries. The surface of the tooth is irradiated with a laser beam for about 1 to about 400 seconds at a power ranging from about 20 to about 50 watts. After the laser beam irradiation, a dissolution rate-inhibiting agent is applied to the tooth's surface. Typical dissolution rate-inhibiting agents are ethane-1-hydroxy-1, 1-diphosphonate ("EHDP"), other diphosphonates, alkyl ammonium salts, and pharmaceutically acceptable salts thereof. The dissolution rate-inhibiting agents can be used in conjunction with one another or separately. Fluorine compounds or fluoride ions can be incorporated with the dissolution rate-inhibiting agents through a pharmaceutical delivery system.

According to this invention, a laser beam is used in conjunction with the chemical treatment of a tooth in a synergistic combination. The lased and chemically treated tooth is more resistant to the formation of dental caries than a tooth subjected to either treatment alone. Applying the dissolution rate-inhibiting agent after the laser treatment increases the tooth enamel's resistivity to cavity formation surprisingly more than chemical treatment before laser irradiation.

While not limiting the scope of the invention to any particular theory or mechanism of action, the following theoretical considerations may explain the synergistic combination which is observed in the practice of this invention.

It is believed that tooth enamel crystals ("hydroxyapatite" or "HAP") possess two types of sites from which dissolution can occur. The first type of site (the "thermal site") is less resistant to dissolution by acids under conditions typically found in the oral environment than is the second type of site (the "chemical site"). The treatment of tooth enamel by carbon dioxide laser irradiation or by high temperatures (for example, 1200° C. for thirty minutes) eliminates or reduces the thermal sites, leaving only the chemical sites for dissolution to occur. Once the thermal sites have been eliminated, the tooth enamel is chemically treated to eliminate the chemical sites.

According to one explanation, dissolution rate-inhibiting agents, such as EHDP, other diphosphonates, and alkyl ammonium salts, either separately, in conjunction with one another, or in conjunctin with fluoride ion (F−), eliminate or reduce the second type of dissolution site. A tooth receiving both laser and chemical treatment thus has both types of dissolution sites eliminated or reduced and is consequently much more resistant to decay.

Lasers useful in the present invention are those which generate sufficient power to increase the acid resistivity of tooth enamel. These lasers include carbon dioxide lasers, argon lasers and tunable lasers which can be tuned to create a laser beam similar in wavelength and power the to laser beam produced by a ($CO_1$) laser. However, carbon dioxide lasers are preferred.

The instant invention typically utilizes laser beam irradiation within the power range of between about 20 and about 50 watts. The beam is typical applied to the tooth's surface for a duration within the range of from about one to about 400 seconds. Both power and exposure interval selected for the laser beam irradiation of intact teeth should avoid damage to the healthy tooth, gums and oral cavity. Laser irradiation times as short as one second significantly slow the dissolution rate of the tooth enamel (See FIG. 2).

A tooth may be laser-irradiated by use of a carbon dioxide laser in conjunction with a fiber optic cable. The fiber optic cable should preferably be of low cross-sectional area so that it can be ued to treat the tooth surfaces between the adjacent teeth. Such an arrangement can also be used to treat the pits and fissures of the molars. A device similar to that disclosed in U.S. Pat. No. 4,273,535 to Yamamoto et al., the contents of which are incorporated by this reference, is useful for this invention, although it is contemplated that a carbon dioxide laser should ordinarily replace the Q-switched continuous excitation Nd:YAG laser disclosed.

The dissolution rate-inhibiting agents of the present invention are typically chemicals which can be used separately or in conjunction with one another, or in conjunction with fluorine to reduce the dissolution rate of a tooth. Ideally such chemicals are non-toxic, soluble in saliva, and compatible with other components of the pharmaceutical delivery system which is used to apply the dissolution rate-inhibiting agent to the tooth.

A preferred dissolution rate-inhibiting agent is EHDP. Pharmaceutically acceptable salts of EHDP useful in the invention include the sodium, trisodium, and disodium salts. Salivary concentrations of EHDP greater than about 0.00001 molar are useful in the invention, although concentrations greater than 0.001 molar are preferred to obtain the greatest reduction in the dissolution rate of the tooth.

Other dissolution rate-inhibiting agents include long-chained (i.e., generally greater than about four carbon atoms per chain) alkyl ammonium compounds, other diphosphonates, and their salts. Mixtures of these agents may also be useful.

Pharmaceutical delivery systems useful in the present invention include those which allow for contact of the particular dissolution rate-inhibiting agent with a previously lased tooth. Examples of such delivery systems include mouthwashes, toothpastes, and chewing gum. In each case, the dissolution rate-inhibiting agent should be present in a concentration to ensure that upon normal use of the delivery system, the agent will be present in the saliva at a sufficient concentration to decrease the dissolution rate of a tooth. Continued application of the dissolution rate-inhibiting agent, for example, on a delay basis, enhances the dissolution-rate inhibition of the tooth enamel.

In an alternative embodiment, the dissolution rate-inhibiting agent is brushed onto the tooth's surface.

DETAILED DESCRIPTION OF THE ILLUSTRATED EMBODIMENT

Figure 1:
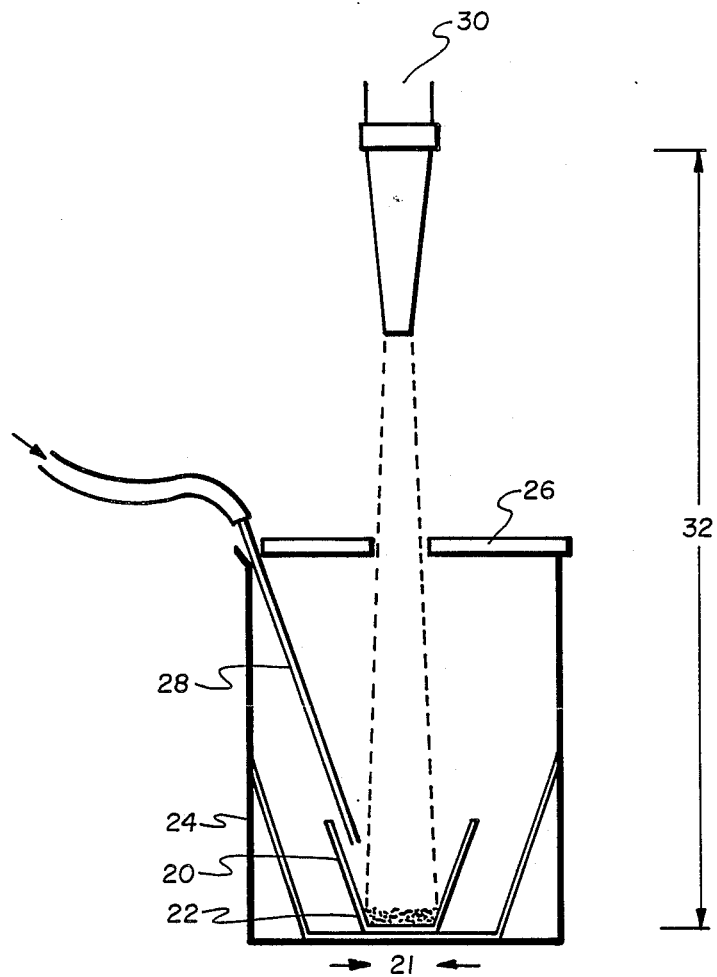
FIG. 1 is a stylized schematic view of hydroxyapatite samples undergoing laser treatment.
Figure 2:
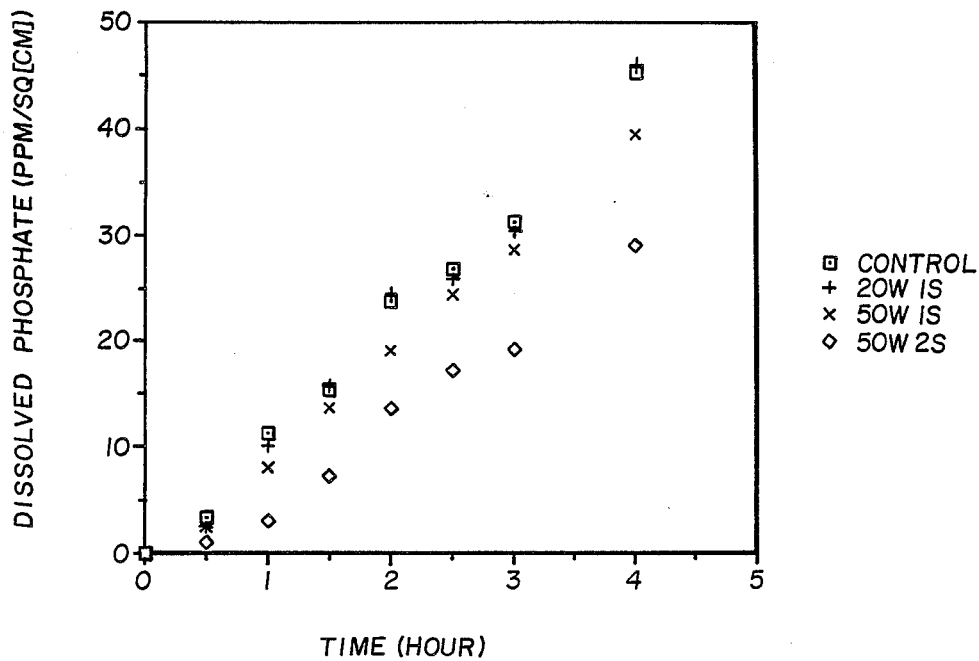
FIG. 2 is a graph of dissolution profiles (6 HR) of lased human enamel blocks.

As shown in FIG. 1, a platinum crucible 20 with a bottom diameter 21 of 14 mm containing 500 mg of HAP sample 22 is placed into a porcelain crucible 24 with plastic cover. Nitrogen gas (that is previously bubbled through water at 25° C.) passes into the crucible via a platinum tube 28 at a rate of 1-1.5 standard liter per minute. During an experiment, the HAP crystals are irradiated by $CO_2$ laser 30 (Sharplan 734), wavelength =10.6 microns, with power ranging from 20 to 50 watts for a period of 10 to 400 seconds from a distance 32 of 37 cm. The HAP sample 22 is uniformly irradiated by alternating the stirring of HAP sample 22 with laser treatment (5 to 20 times) during the course of irradiation.

EXAMPLES

For purposes of the following Examples, the following described materials were used:

Hydroxyapatite ("HAP")

Pure phosphoric acid was added at a slow controlled rate to a boiling, carbon dioxide-free, calcium oxide suspension in a Teflon flask. By applying a screw clamp to the polyethylene tubing section downstream from the Teflon flask, the boiling temperature of water was controlled at approximately 105° C. The sample prepared at this temperature was labeled as "UU-5." The resulting precipitate was digested for two weeks in the boiling-reactant solution with a constant bubbling of nitrogen ($N_2$) ($CO_2$ free). The residue was centrifuged, and the supernatant liquid was decanted. Freshly boiled double-distilled water was then added and the suspension was stirred and centrifuged again. This same procedure was repeated threr times. The final residue was then dried at 110° C. over night. Those skilled in the art will recognize that HAP treated in this manner is nearly identical to human dental enamel.

Solutions

Calculated amounts of acetic acid and sodium acetate stock solutions were used to make up the pH=4.5, 0.1 M acetate buffer solution. The ionic strength of all buffer solutions was adjusted at 0.50 with sodium chloride. The pH of each solution was measured to an accuracy of +0.01 using a digital pH-meter (Altex model 4500). Partial saturated buffer solutions were prepared adding predetermined amounts of calcium chloride or sodium dihydrogen phosphate to the buffer.

Ethane-1-Hydroxy-1,1-Diphosphonic Acid (EHDP)

EHDP was etidronate disodium, and was provided as a gift by Norwich Eaton Pharmaceuticals, Inc. The purity of the EHDP was 99.8%.

Heat Treatment of HAP

A platinum crucible containing 3 grams (g) of UU-5 sample was placed in the furnace (Thermolyne, 10500 furnace) at 1200° C. for 30 minutes. A mixture of nitrogen gas and water vapor from a boiling flask was passed via platinum tubing into the furnace at a rate of 1-1.5 liters per minute.

Characterization

All HAP samples were checked by powder X-ray diffraction analysis (XRC 2500, NIMS). Infrared absorption spectroscopy (Microlab 620 MX, Beckman Co. Ltd.) and FTIR (FTS-40 Digilab) by means of potassium bromide (KBr) disk method were employed to obtain the infrared spectra of the HAP samples.

Dissolution

Hydroxyapatite in clumps was broken down by light grinding until no visible lumps were present. Exactly 20 mg of HAP was suspended in 25 ml of double-distilled water in a 80 ml water-jacketed (30° C.) reaction vessel. This suspension was magnetically stirred for 20 seconds at 600 rpm after being sonified for 60 seconds to produce a milky suspension. After sonification, stirring was resumed and 25 ml of the pH =4.5 acetate buffer solution dissolution medium (double concentration) was added to the suspension. Addition and mixing was completed 1 to 2 seconds and the pH at this point was recorded to be at 4.50 ±0.01. Samples of 1.5 ml were withdrawn at predetermined times with an Eppendorf pipet during the dissolution experiment and immediately passed through a Millipore filter paper (GSU) with a pore size of 0.22 microns. Sampling and filtering were completed within 4 to 6 seconds. The filtrate was analyzed for phosphate.

*Phosphate Analysis.* Phosphate concentration in dissolution medium was determined by the method as described by Gee et al., *Anal. Chem.*, 26, 1487 (1954), the contents of which are incorporated by this reference.

EXAMPLE 1

Five samples were used and each was treated differently in the device of FIG. 1. Sample 1 of the UU-5 (synthetic HAP) went untreated. Sample 2 was irradiated with the $CO_2$ laser at 20 watts for ten seconds. Sample 3 was treated with the $CO_2$ laser at 50 watts for 50 seconds. Sample 4 was treated with the $CO_2$ laser at 50 watts for 200 seconds. Sample 5 was heat treated at 1220° C. for 30 minutes.

The effect of the various treatments on the HAP samples' dissolution rates was then measured. The following results were obtained:

| SAMPLE | INITIAL DISS. RATE (ppm/sec) | SURFACE AREA ($m^2/g$) | CORRECTED INITIAL DISS. RATE (ppm/sec $m^2$) |
|---|---|---|---|
| 1 | 7.78 | 14.57 | 0.534 |
| 2 | 4.51 | 14.01 | 0.322 |
| 3 | 2.13 | 9.12 | 0.234 |
| 4 | 0.51 | 5.77 | 0.089 |
| 5 | 0.04 | 0.25 | 0.159 |

As is shown by this table, the dissolution rates of HAP decrease significantly with both increasing laser time and power (as measured in watts). This retardation of dissolution is apparently due to the decreased specific surface area.

EXAMPLE 2

A new Sample 6 was prepared which was treated with the $CO_2$ laser at 50 watts for 400 seconds. Samples 1 and 5 from example 1, and Sample 6 were then dissolved in varying concentrations of EHDP, and the following normalized initial dissolution rates (percent of normal) were obtained:

| Concentration of EHDP (Molar) | Sample 1 | Sample 6 | Sample 5 |
|---|---|---|---|
| 0 (normal) | 100.0 ± 2.3 | 100.0 ± 1.7 | 100.0 ± 4.2 |
| 0.00001 | 67.5 ± 1.9 | 30.4 ± 1.2 | 0.0 ± 3.2 |
| 0.0001 | 26.6 ± 2.1 | 25.3 ± 1.5 | 0.0 ± 2.4 |
| 0.001 | 7.1 ± 1.8 | 0.2 ± 0.6 | 0.0 ± 1.5 |
| 0.003 | 4.1 ± 1.2 | 0.0 ± 0.7 | 0.0 ± 2.2 |

The lased HAP has a much slower dissolution rate than the untreated HAP. The greater the concentration of EHDP, the slower the dissolution rate.

EXAMPLE 3

Human dental enamel was laser irradiated as the HAP was in Examples 1 and 2 but for only two seconds at 50 watts. The solubility of the lased enamel was 58% of that of the unlased dental enamel. The dissolution of human dental enamel at pH 4.5 corresponds to the solubility of the enamel.

Reference herein to certain embodiments or specific details is not intended to limit the scope of the appended claims.

What is claimed is:

1. A method of treating a tooth comprising: irradiated said tooth with a laser beam at a power ranging from about 20 watts to about 50 watts for a period of time ranging from about 1 second to about 400 seconds; and thereafter applying ethane-1-hydroxy-1, 1 diphosphonic acid as a dissolution rate-inhibiting agent to said tooth, said dissolution rate inhibiting agent being in a sufficient concentration to decrease the dissolution rate of that tooth.

2. The method according to claim 1 wherein said laser beam has been generated by a carbon dioxide laser.

3. The method according to claim 2 wherein said dissolution rate-inhibiting agent is present in a saliva solution at a concentration of at least about 0.00001 molar.

4. The method according to claim 3 wherein said ethane-1-hydroxy-1,1-diphosphonic acid is applied to said tooth in a pharmaceutical delivery system containing a pharmaceutically acceptable salt of ethane-1-hydroxy-1,1-diphosphonic acid.

5. The method according to claim 4 wherein said pharmaceutical delivery system includes a fluorine compound.

6. The method acording to claim 4 wherein said pharmaceutical delivery system is a mouthwash.

7. The method according to claim 4 wherein said pharmaceutical delivery system is a chewing gum.

8. The method according to claim 4 wherein said pharmaceutical delivery system is a toothpaste.

* * * * *

UNITED STATES PATENT AND TRADEMARK OFFICE
CERTIFICATE OF CORRECTION

PATENT NO. : 4,877,401

DATED : OCTOBER 31, 1989

INVENTOR(S) : WILLIAM I. HIGUCHI ET AL.

It is certified that error appears in the above-identified patent and that said Letters Patent is hereby corrected as shown below:

COLUMN 1, LINE 5, AFTER THE TITLE AND BEFORE THE BACKGROUND OF THE INVENTION", PLEASE INSERT:

---THIS INVENTION WAS MADE WITH GOVERNMENT SUPPORT UNDER GRANT NUMBER NIH R01-DE06569 AWARDED BY THE DEPARTMENT OF HEALTH & HUMAN SERVICES/INSTITUTE OF HEALTH. THE GOVERNMENT HAS CERTAIN RIGHTS IN THE INVENTION.---

Signed and Sealed this

Sixth Day of April, 1993

*Attest:*

STEPHEN G. KUNIN

*Attesting Officer*     *Acting Commissioner of Patents and Trademarks*